United States Patent [19]

Lee, Jr.

[11] Patent Number: 4,964,320

[45] Date of Patent: Oct. 23, 1990

[54] METHOD OF FORMING A BEADED TRANSFIXION WIRE

[75] Inventor: Harry E. Lee, Jr., Southaven, Miss.

[73] Assignee: Engineering & Precision Machining, Inc., Memphis, Tenn.

[21] Appl. No.: 402,081

[22] Filed: Sep. 1, 1989

Related U.S. Application Data

[62] Division of Ser. No. 288,426, Dec. 22, 1988.

[51] Int. Cl.$^5$ .......................... B23B 1/00; B23B 5/00; B23B 13/02
[52] U.S. Cl. ........................................ 82/1.11; 82/11; 82/127; 82/164
[58] Field of Search ................... 82/1.11, 11, 127, 164

[56] References Cited

U.S. PATENT DOCUMENTS

| | | | |
|---|---|---|---|
| 320,992 | 6/1885 | Woerd | 82/124 |
| 2,377,383 | 6/1945 | Slovak | 82/127 |
| 3,596,545 | 6/1969 | Eisenhardt | 82/127 |
| 3,664,215 | 5/1972 | Selby | 82/127 |
| 3,703,112 | 11/1972 | Selby | 82/127 |
| 3,915,162 | 10/1975 | Miller | 128/92 |
| 4,068,546 | 1/1978 | Werkmeister | 128/92 |
| 4,615,338 | 10/1986 | Ilizarov et al. | 128/92 |
| 4,655,105 | 4/1987 | Maxwell et al. | 82/1.11 |

FOREIGN PATENT DOCUMENTS

| | | | |
|---|---|---|---|
| 643131 | 5/1984 | Switzerland | 128/92 YE |
| 827051 | 5/1981 | U.S.S.R. | 128/92 ZW |

OTHER PUBLICATIONS

Tool and Manufacturing Engineers Handbook (3rd Edition), pp. 5-121 -5-127. Marubeni Citizen-Cincom, Inc. Brochure; Citizen Watch Co., LTD
Marubeni Citizen-Cincom, Inc. Brochure.
Citizen Watch Co., LTD catalog No. 150E, 1986.
Citizen Watch Co., LTD Catalog No. 121E, 1985.
Star Micronics Co., LTD, Catalog RNC-16.
Star Micronics Co., LTD Catalog KNC-16.20.
Star Micronics Co., LTD, Catalog KNC-25/32.
Howe Sound Co. Catalog, 3 pages, 1964.
Metal Handbook 9th Edition, vol. 13, Corrosion, 16 pages.

*Primary Examiner*—William E. Terrell
*Attorney, Agent, or Firm*—Walker & McKenzie

[57] ABSTRACT

A method of forming a beaded transfixion wire for orthopedic uses. The beaded transfixion wire includes an elongated wire formed of an implant grade material. A bead is provided on the elongated wire intermediate the opposite ends thereof. The bead extends outwardly beyond the outer surface of the elongated wire and is integral therewith.

In forming the beaded transfixion wire the solid bar stock is rotatably fed past a cutting tool to turn down a portion of the bar stock to a selected daiameter to provide a first portion of an elongated wire. The first portion of the elongated wire is fed into a tube for stabilizing the first portion against any whipping motion. The solid bar stock is continued to be rotated past the cutting tool while at the same time a bead is profiled from the solid bar stock with the cutting tool. After the bead has been formed in the bar stock another portion of the bar stock is turned down to the selected diameter to provide a second portion of the elongated wire having the selected diameter.

8 Claims, 2 Drawing Sheets

METHOD OF FORMING A BEADED TRANSFIXION WIRE

CROSS-REFERENCE TO RELATED APPLICATION

This is a division of my application Ser. No. 07/288,426 pending, filed Dec. 22, 1988, entitled "Beaded Transfixion Wire and Method of Forming Same".

BACKGROUND OF THE INVENTION

1. Field of the Invention:

The present invention relates, in general, to the method of forming beaded transfixion wires or pins for orthopedic uses.

2. Information Disclosure Statement:

Heretofore, beaded transfixion wires or pins have been formed from two parts, i.e., a wire and a bead. The prior art methods of forming the beaded transfixion wire or pin included the steps of providing a hole in the bead and fitting the bead on the wire by extending the wire through the hole. The next step was then to fix the bead onto the wire by silver soldering, welding, crimping or the like. The final steps were to provide a drill point on one end of the beaded transfixion wire, and then to finish the product by polishing same, as for example to smooth out the soldering or welded joint between the wire and the bead.

So-called Swiss-type for sliding-headstock machines are known in the prior art and some include a tube feeder, sliding-headstock, a guide bushing having a collet, a cutting tool, and a support which the end of the stock engages to eliminate deflection. Although such machines have been known in Europe for many years and the problems in manufacturing transfixation wires or pins formed from two parts have also been known for a long time, due to the small diameter and length of such wires or pins, prior to the present invention no thought has been given to forming the wires or pins with the bead being integral with the wire or attempting to form same on such sliding-headstock machines. The following publications provide examples of such sliding-headstock machines: *Tool and Manufacturing Engineers Handbook* (3rd Edition), pages 5–121–5–127; Marubeni Citizen-Cincom Inc. brochure; Citizen Watch Co., LTD. catalog No. 150E, 1986; Citizen Watch Co., LTD. catalog No. 121E, 1985; Star Micronics Co., LTD. catalog RNC-16; Star Micronics Co., LTD. catalog KNC-16.20; and Star Micronics Co., LTD. catalog KNC-25/32.

Ilizarov et al U.S. Pat. No. 4,615,338 issued 10/7/86 shows one type of automatic compression-distraction apparatus with which the beaded transfixion wire of the present invention may be used.

SUMMARY OF THE INVENTION

The present invention is directed towards providing an improved, efficient, and economical method of forming a beaded transfixion wire or pin for orthopedic uses.

One of the objects of the present invention is to provide a method for forming such a beaded transfixion wire or pin in which the bead is integral with the elongated wire, i.e., the product of the present invention is formed from a single solid piece of material so that rather than being of two parts, as prior beaded transfixion wires or pins, the bead and elongated wire comprise a single unitary and solid piece.

A further object is to provide a method for forming such a beaded transfixion wire which can be F.D.A. approved as opposed to some of the previous beaded transfixion wires which were silver soldered.

A further object is to provide a method for forming a beaded transfixion wire or pin which is stronger than previous devices such as those in which the beads were pressed onto the elongated wire or were welded.

The beaded transfixion wire or pin formed by the method of the present invention includes an elongated wire formed of an implant grade material and terminating in a first end and a second opposite end with said elongated wire having an outer surface, a bead provided on said elongated wire intermediate said first and second ends, and bead extending outwardly beyond said outer surface of said elongated wire and being integral with said elongated wire.

The method of the present invention includes the steps of (1) rotatably feeding solid bar stock at a selected advancement rate past a cutting tool fixed in a first position to turn down a portion of said bar stock to a selected diameter to provide a first portion of said elongated wire having said selected diameter; (2) feeding said first portion of said elongated wire into tube means for stabilizing said first portion against any whipping motion; (3) continuing to rotatably feed said solid bar stock past said cutting tool while at the same time profiling a bead from said solid bar stock by moving said cutting tool outwardly and inwardly relative to the direction of travel of said bar stock; and (4) after said bead has been formed in said bar stock and with said cutting tool positioned in said first position turning down another portion of said bar stock to said selected diameter to provide a second portion of said wire having said selected diameter.

DESCRIPTION OF THE PREFERRED EMBODIEMT

Figure 1:
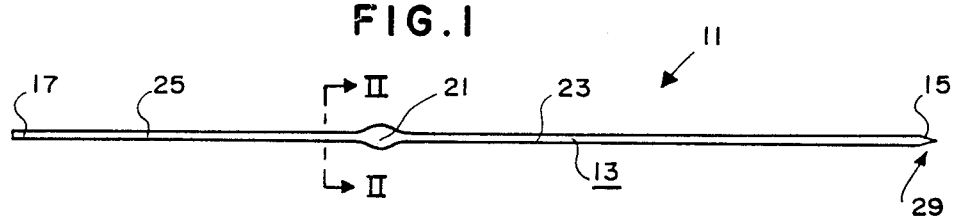
FIG. 1 is a side elevational view of the beaded transfixion wire formed by the method of the present invention.
Figure 2:
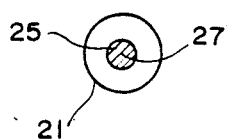
FIG. 2 is an enlarged sectional view taken as on the line II—II of FIG. 1.
Figure 3:
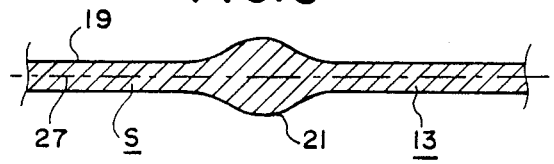
FIG. 3 is an enlarged fragmentary sectional view of the beaded transfixion wire formed by the method of the present invention taken as on a plane through the longitudinal centerline thereof.

The beaded transfixion pin or wire 11 formed by the method of the present invention includes an elongated wire 13 formed of a suitable implant grade material, as for example, titanium or stainless steel S. Elongated wire 13 terminates in a first end 15 and a second opposite end 17, and has a outer surface 19. Beaded transfixion wire 11 also includes a bead 21 provided on elongated wire 13 intermediate first end 15 and second end 17. Bead 21 extends outwardly beyond outer surface 19 and is integral with elongated wire 13. It should be pointed out that when bead 21 is described herein as being "integral" with elongated wire 13 it is to be understood as meaning that the bead 21 is formed from the same solid piece of material as elongated wire 13 to provide beaded transfixion wire 11 as a single unitary and soldi piece. In other words, it is one single piece of materal as opposed to being formed of two parts as with prior art pins which comprised a bead with a hole therein through which the wire extends and with the bead being fixed onto the wire with solder, crimping or the like.

For purposes of clarity and understandeing the portion of elongated wire 11 between bead 21 and first end 15 is herein designated as first portion 23 and the portion of elongated wire 11 between bead 21 and second end 17 is herein desingated as second portion 25.

Elongated wire 13 is preferably circular in cross section with the diameter of the elongated wire being preferably 1.5 millimeters or approximately of that diameter. Bead 21 is also preferably circular in cross section with the diameter of the bead being preferably 4.5 millimeters or approximately of that diameter, and preferably being concentric with respect to the longitudinal axis 27 of elongated wire 13. Beaded transfixion wire 11 is of any suitable overall length, as for example 15⅝ inches (396.88 millimeters). Bead 21 is of any suitable length, as for example ¼ inch (6.35 millimeters) with the bead preferably being closer to one end of the beaded transfixion wire than the other, as for example, first portion 23 being 9¼ inches (234.95 millimeters) and second portion 25 being 6⅛ inches (155.58 millimeters). The reason for bead 21 being closer to second end 25 than to first end 15 will be better understood in the description to follow later in the specification of the use of the beaded transfixion wire 11 formed by the method of the present invention. Beaded transfixion wire 11 is preferably provided with a suitable drill point 29 at first end 15 for a purpose later to be described.

Figure 4:
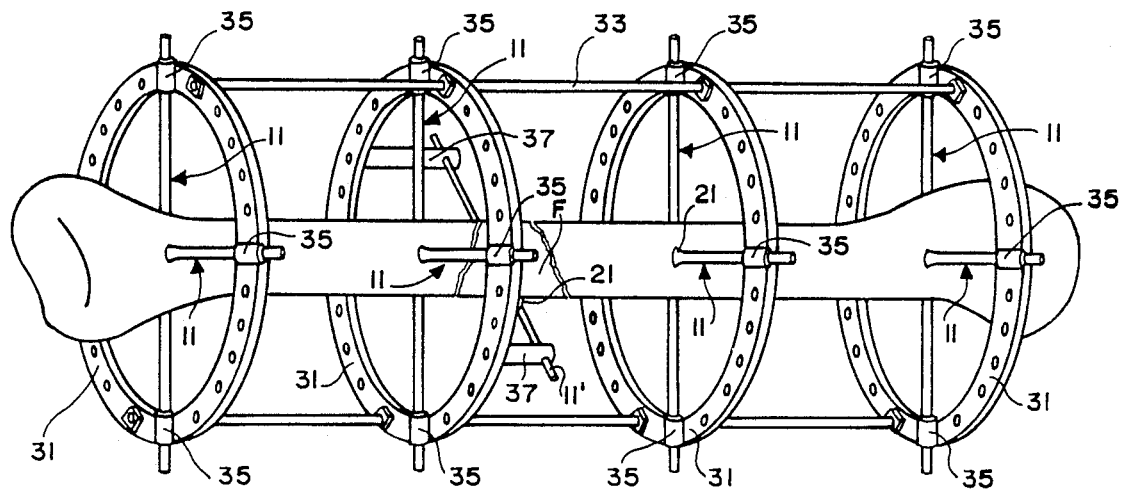
FIG. 4 is a perspective view showing one application of the beaded transfixion wire formed by the method of the present invention.

The beaded transfixion wires 11 formed by the method of the present invention are adapted for various orthopedic uses in the same manner as previous beaded transfixion wires or pins have been used. See for example, the various uses of pins in U.S. Pat. No. 4,615,338, and see FIGS. 4 and 5 of the drawings herein. Thus, in FIG. 4 there is shown beaded transfixion pins or wires 11 which are used in reducing fractures in the bone B. The rings 31 are fastened together with rods 33 and each of the beaded transfixion wires 11 are inserted into the bone B as by being drilled thereinto with a drill, not shown, which causes the drill point 29 to penetrate the bone until the bead 21 engages the bone to stop the penetration of the beaded transfixion wire 11 into the bone. The beaded transfixion wires 11 are then tensioned and secured to rings 31 by gripping devices 35 well known to those skilled in the art, and the fracture is then reduced by applying the proper compression in a manner well known to those skilled in the art. Also, in the case of the reduction of a bone fragment an additional beaded transfixion wire 11 shown as at 11' may be provided and supported from one of the rings 31 by suitable means as supports 37. The bone fragment F can then be manupulated as desired to move the fragment into place. From the foregoing, it will be understood that bead 21 is preferably closer to second end 17 than to first end 15 to compensate for the thickness of the bone. Also, it will be understood that the flesh, skin, and remaining portions of the persons's body have been omitted for purposes of illustration.

Figure 5:
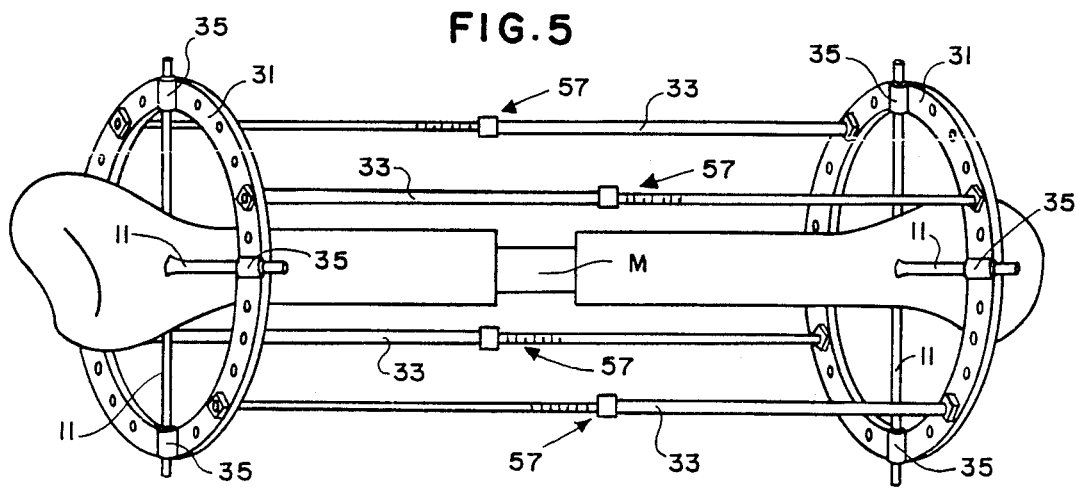
FIG. 5 is a perspective view showing another application of the beaded transfixion wire formed by the method of the present invention.

In FIG. 5 is shown an example of bone elongation in which beaded transfixion wires or pins are used. This is a process which was developed by Dr. Gavrill A. Ilizarov of the Soviet Union and further information regarding this type of procedure may be found in Gavrill et al U.S. Pat. No. 4,615,338. In FIG. 5 there is shown the bone after a corticotomy has been performed in which a section of the cortex of the bone has been removed exposing the medulla M. After as optimum time has elapsed the bone is then ready for the start of the lengthening process. Also, it will be noted that rods 33 are provided with adjustment means 57 for use in the extension process.

The preferred method of the present invention for forming beaded transfixion wires 11, in general comprises the steps of: (1) feeding solid bar stock B of a suitable implant grade material, as titanium or stainless steel S, from a tube feeder 41 into a sliding head stock device 43 where the bar stock B is continuously rotated as indicated by the arrow 45 and advanced longitudinally along a line of travel in the direction indicated by the arrow 46; (2) after leaving sliding head stock device 43, feeding the rotating and advancing bar stock B through a guide bushing 49 and past a cutting tool 47 fixed in a first position to turn down a portion of bar stock B to a selected diameter to provide first portion 23 of elongated wire 13 having a selected diameter, as for example, 1.5 millimeters; (3) feeding first portion 23 of elongated wire 13 into a hollow tube 51 for stabilizing first portion 23 against any whipping motion; (4) continuing to rotatably feed solid bar stock B past cutting tool 47 while at the same time profiling a bead 21 from solid bar stock B by moving cutting tool 47 outwardly and inwardly relative to the direction of travel 46 of bar stock B; and (5) after bead 21 has been formed in bar stock B and with cutting tool 47 positioned in said first position, turning down another portion of bar stock B to said selected diameter to provide a second portion 25 of elongated wire 13 having said selected diameter.

Except for tube 51, the above mentioned components, namely, tube feeder 41, sliding-headstock device 43, cutting tool 47, and guide bushing 49 are well known to those skilled in the art and being components of a so-called Swiss-type or sliding-headstock machine, the operation of these components, except for the forming of a beaded transfixion wire on such a machine and the feeding of the first portion of the elongated wire into tube 51, is well known to those skilled in the art.

Figure 6:
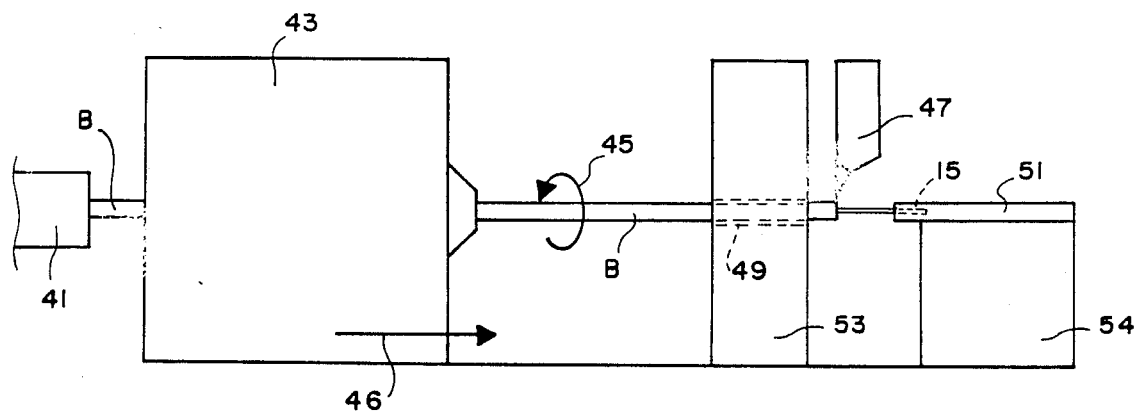
FIGS. 6–8 are diagrammatic views illustrating steps of the method of the present invention.

More specifically, from the tube feeder 41 the bar stock B is fed into the sliding-headstock device 43 which has mechanisms therein, not shown, well known to those skilled in the art, which cause the bar stock B to rotate about its longitudinal axis and at the same time the sliding-headstock slides to the right, as shown by the arrow 46 in FIG. 6 to move the rotating bar stock B to the right therewith so that the bar stock advances past cutting tool 47 which is in a selected fixed first position to turn down a portion of bar stock B to provide a first portion 23 of the elongated wire 13.

Between sliding-headstock device 43 and cutting tool 47 is preferably provided a stationary guide bushing housing 53 that houses guide bushing 49 which permits bar stock B to turn and to advance yet holds the bar stock at a place adjacent and upstream of cutting tool 47 rigidly against movement out of the line of travel of the bar stock B in a manner well known to those skilled in the art.

The end 15 of first portion 23 is fed into tube 51 (see FIG. 6) which is fixedly supported by suitable means, such as welding or the like, on a sliding tailstock support 54, which tailstock support is well known to those skilled in the art.

As solid bar stock B is continued to be rotated and advanced past cutting tool 47 a bead 21 is profiled, i.e., formed from the bar stock by moving the cutting tool outwardly and inwardly relative to the direction of travel of the bar stock. This movement is carried out by suitable means, not shown, but well known to those skilled in the art and may be done by computer control to cause the cutting tool to move at the appropriate time and by an appropriate amount.

Figure 7:
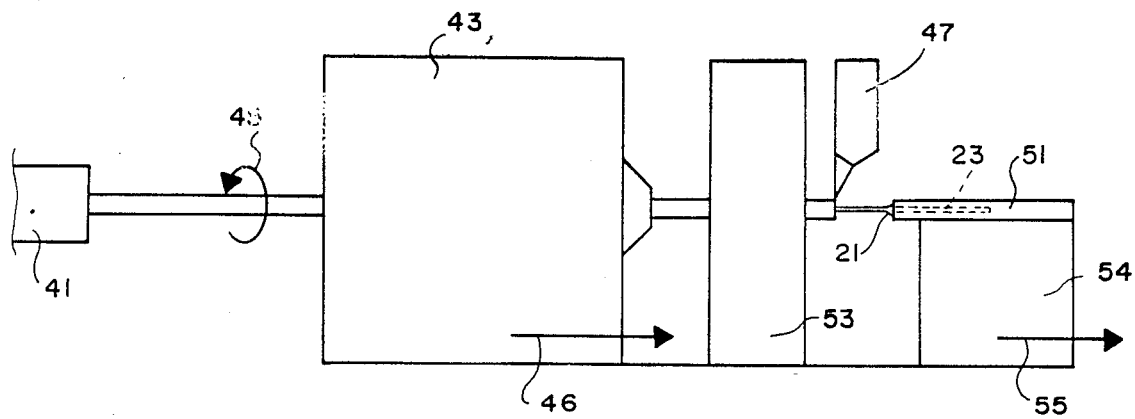
Figure 8:
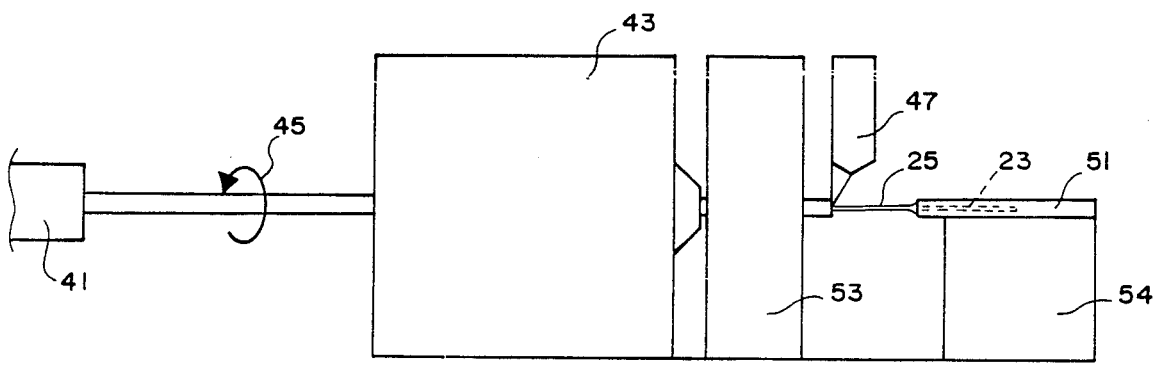

After bead 21 has been formed in bar stock B and with the cutting tool 47 returned back to said first position, cutting tool 47 begins to turn down second portion 25 at the same selected diameter as said first portion 23. At the same time the first portion 23 continues to be fed into tube 51 until bead 21 abuts the end of the tube (see FIG. 7). At this time the first portion 23 is completely into tube 51 which stabilizes the first portion against any whipping motion. Also, at this time the sliding tailstock support 54 begins to move with the bead 21 and first portion 23 as shown by the arrow 55, and continues such movement until the cutting tool 47 has completed the forming of second portion 25. This movement is accomplished by suitable means, not shown, well known to those skilled in the art and preferably includes computer control means. After second portion 25 has been formed, the second portion is detached form bar stock B by cutting the material with cutting tool 47 as by causing the cutting tool to be moved inwardely by suitable means well known to those skilled in the art. FIG. 8 shows the various components just before this last mentioned detachment step is performed.

It will be understood that in the heretofore described preferred method in which the bead 21 abuts the end of the 51, the inside diameter of tube 51 is slightly greater than the outside diameter of first portion 23 but is less than the diameter of bead 21 so that only first portion 23 will move completely into tube 51 and will be stabilized against any whipping motion. However, if desired, the inside diameter of tube 51 may be slightly greater than the outside diameter of bead 21 in which case the bead as well as first portion 23 and a part of second portion 25 may move into tube 51, and tailstock support 54 may remain stationary with the bead 21 stabilizing the beaded transfixion wire 11 against whipping motion.

Finally, after beaded transfixion wire 11 has been parted from the bar stock B, a drill point 29 is provided on first end by any suitable means or method well known to those skilled in the art.

Although the present invention has been described and illustrated with respect to a preferred embodiment and a preferred use therefor, it is not to be so limited since modifications and changes can be made therein which are within the full intended scope of the invention.

I claim:

1. A method for forming a beaded transfixion wire for orthopedic uses comprising the steps of:
    (a) rotatably and longitudinally feeding solid bar stock along a line of travel at a selected advancement rate past a cutting tool fixed in a first position to turn down a portion of said bar stock to a selected diameter to provide a first portion of an elongated wire having said selected diameter;
    (b) while rotatably and longitudinally feeding said solid bar stock along said line of travel past said cutting tool feeding said first portion of said elongated wire into tube means for stabilizing said first portion against any whipping motion;
    (c) continuing to rotatably feed said solid bar stock past said cutting tool while at the same time profiling a bead from said solid bar stock by moving said cutting tool outwardly and inwardly relative to the direction of travel of said bar stock; and
    (d) after said bead has been formed in said bar stock and with said cutting tool positioned in said first position and while said first portion of said elongated wire is continuously rotated in said tube means turning down another portion of said bar stock to said selected diameter to provide a second portion of said elongated wire having said selected diameter.

2. The method of claim 1 wherein the inside diameter of said tube means is less than the diameter of said bead and greater than the diameter of said first portion of said elongated wire and wherein after said bead has been formed in said bar stock and after said first portion is fed into said tube means and advanced to a point where said bead is adjacent said tube means, advancing said tube means at substantially the same rate as the advancement rate of said bar stock past said cutting tool.

3. The method of claim 1 wherein said tube means is held in a stationary position; wherein the inside diameter of said tube means is slightly greater than the diameter of said bead means; and wherein after said bead has been formed in said bar stock and after said first portion is fed into said tube means, continuing to advance said first portion and said bead therewith into said tube means.

4. The method of claim 3 wherein after forming portions of said second portion of said wire, advancing said second portion of said wire into said tube means.

5. The method of claim 1 wherein guide bushing means holds said bar stock at a place adjacent and upstream of said cutting tool rigidly against movement out of the line of travel of said bar stock.

6. A method for forming a beaded transfixion wire for orthopedic uses comprising the steps of:
    (a) feeding solid bar stock from a tube feeder into a sliding head stock means where the bar stock is continuously rotated and advanced longitudinally along a line of travel;
    (b) after leaving said sliding head stock means, feeding the rotating and advancing bar stock past a cutting tool fixed in a first position to turn down a portion of said bar stock to a selected diameter to provide a first portion of an elongated wire having said selected diameter;
    (c) holding said bar stock by guide bushing means at a place adjacent and upstream of said cutting tool rigidly against movement out of the line of travel of said bar stock;
    (d) feeding said first portion of said elongated wire substantially completely into tube means for stabilizing said first portion against any whipping motion;
    (e) continuing to rotatably feed said solid bar stock past said cutting tool while at the same time profiling a bead from said solid bar stock by moving said cutting tool outwardly and inwardly relative to the direction of travel of said bar stock; and (f) after said bead has been formed in said bar stock and with said cuttin tool positioned in said first position turning down another portion of said bar stock to said selected diameter to provide a second portion of said elongated wire having said selected diameter and with the combined lengths of said first and second portions of said elongated wire having a length to diameter ratio of at least as large as 100 to 1.

7. The method of claim 6 wherein after said second portion has been formed, detaching said second portion from said bar stock by cutting the material with said cutting tool.

8. The method of claim 7 which includes, after the detachment of said second portion, the step of providing a drill point on one end of said beaded transfixion wire.

* * * * *